United States Patent [19]

Passaro

[11] 4,398,091
[45] Aug. 9, 1983

[54] TEMPERATURE COMPENSATED GAS ANALYZER

[75] Inventor: Robert E. Passaro, Walnut Creek, Calif.

[73] Assignee: Andros Analyzers Incorporated, Oakland, Calif.

[21] Appl. No.: 295,570

[22] Filed: Aug. 24, 1981

[51] Int. Cl.³ .......................................... G01N 21/26
[52] U.S. Cl. ................................................... 250/343
[58] Field of Search ............... 250/343, 344, 345, 346, 250/373, 432 R, 435; 356/51, 437

[56] References Cited

U.S. PATENT DOCUMENTS

| | | | |
|---|---|---|---|
| 3,790,797 | 2/1974 | Sternberg et al. | 250/345 |
| 4,013,260 | 3/1977 | McClatchie et al. | 250/343 |
| 4,153,837 | 5/1979 | Ross | 250/343 |
| 4,346,296 | 8/1982 | Passaro et al. | 250/343 |

Primary Examiner—Janice A. Howell

Attorney, Agent, or Firm—Fitch, Even, Tabin & Flannery

[57] ABSTRACT

An infrared gas analyzer is described wherein infrared energy is directed from a suitable source through a sample cell, the infrared energy being interrupted at a predetermined frequency. Infrared energy of a preselected wavelength causes a detector for each monitored gas to produce a signal proportional to the infrared energy passing through the sample cell and having a frequency corresponding to the predetermined frequency. Each preselected wavelength corresponds to the characteristic absorption wavelength of a preselected gas. A signal processor for the analyzer includes a preamplifier adapted to compensate for temperature variations in the detector while an output amplifier is adapted to compensate for temperature variations in the sample cell in order to provide a more accurate output signal.

5 Claims, 2 Drawing Figures

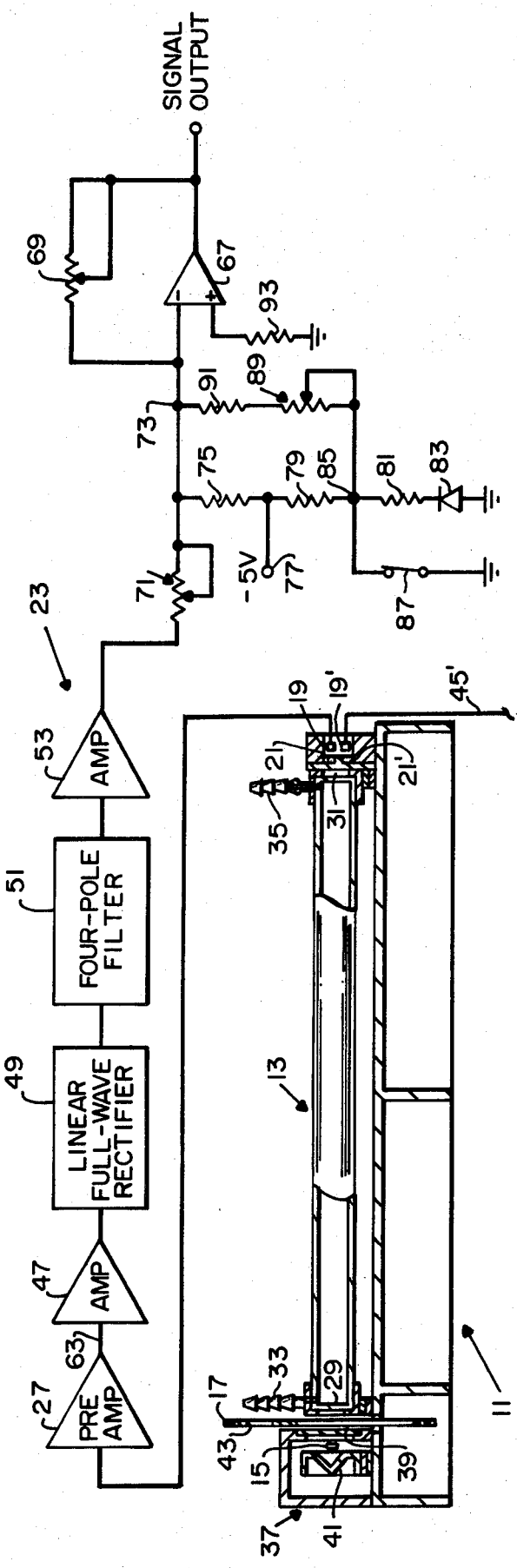
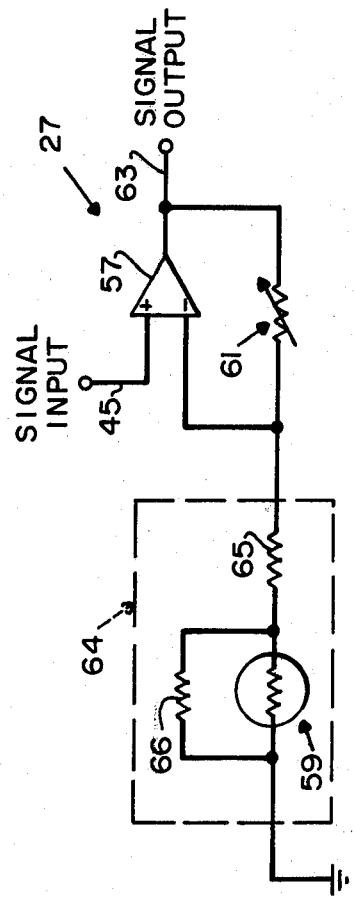
FIG. 1
FIG. 2

TEMPERATURE COMPENSATED GAS ANALYZER

The present invention relates generally to infrared gas analyzers and more particularly to an improved gas analyzer and method of gas analysis including means to compensate for temperature variations in critical components of the analyzer.

Infrared gas analyzers of the type contemplated by the present invention typically employ an infrared source to pass infrared energy through an unknown gas mixture in a sample cell. The energy passing through the sample cell is detected to produce an electrical signal representative thereof. The resulting signal for each gas to be monitored in the analyzer is converted to an output indicating the concentration for the respective gases in the sample cell.

Infrared gas analyzers operate on the principle that various gases exhibit substantial absorption characteristics at specific wavelengths in the infrared radiation spectrum. Gas analyzers of this type are shown and described respectively in U.S. Pat. No. 4,013,260 issued to McClatchie et al., on Mar. 22, 1977 and in application Ser. No. 178,302, filed Aug. 15, 1980 by Passaro et al., now U.S. Pat. No. 4,346,296 issued on Aug. 24, 1982, both assigned to the assignee of the present invention.

Gas analyzers such as those disclosed in the above references employ a beam of infrared energy passing through the sample cell containing an unknown gas mixture, the infrared energy beam being varied by the position of one or more filters in the path of the light beam. Typically, each filter passes only radiation at a characteristic absorption wavelength for a respective gas of interest. One or more additional filters may also be used as reference filters at wavelengths close to but not overlapping the characteristic absorption wavelength for any gas present in the sample cell.

A simplified gas analyzer may also use a stationary filter or multiple filters with associated detectors rather than rotary filter wheel as described above. Such analyzers cause an AC signal to be produced by the detector by periodically interrupting the infrared beam, for example with a rotary chopper.

In any event, gas analyzers of the type described above are used in many applications where it is necessary to determine gas composition within the sample cell with maximum accuracy possible. However, such gas analyzers are susceptible to variations in their output signals for various reasons including variations in ambient temperature which may affect different components of the analyzer. In particular, it has been found that the detector for each gas channel is temperature-sensitive. Accordingly, variations in ambient temperature for the analyzer may cause variations in the output from the detector which will provide an inaccurate indication of each preselected gas in the sample cell. At the same time, temperature variations within the sample cell itself during operation of the analyzer will tend to cause variations in gas density within the sample cell which will similarly produce inaccurate results for the analyzer. In this regard, a typical processing circuit for use in communication with such an analyzer is described in greater detail within the second reference noted above and the disclosure of that reference is incorporated herein as though set out in its entirety.

In any event, there has been found to remain a need for an infrared gas analyzer including means capable of compensating for temperature variations which could otherwise produce inaccurate results for the analyzer.

It is therefore an object of the invention to provide an improved gas analyzer of the type including a source for directing infrared energy through a sample cell containing a gas of unknown composition, means for interrupting the infrared energy for a preselected wavelength and a detector for monitoring infrared energy passing through the sample cell, circuit means for conditioning an output signal from the detector including means for compensating for temperature variations within the detector.

Preferably, the invention contemplates a preamplifier coupled with the output of each detector in the analyzer, the preamplifier including adjustment means for error correction resulting from variations in the ambient or operating temperature of the detector.

It is also an object of the invention to provide circuit means for compensating for variations in the ambient or operating temperature of the sample cell itself. In this regard, the present invention preferably contemplates an output amplifier in the processing circuit for each gas channel including selectively actuated means subject to similar temperature variations as the sample cell, adjustable means being associated with the output amplifier in order to produce offsetting compensation in the output amplifier.

Additional objects and advantages of the invention will be apparent from the following description, having reference to the accompanying drawings wherein:

FIG. 1 is a view, with parts shown in section and other parts shown schematically, of an infrared gas analyzer constructed in accordance with the present invention; and FIG. 2 is a fragmentary view of a circuit component for the analyzer of FIG. 1.

Generally, the nondispersive infrared gas analyzer of the invention, indicated at 11, comprises a sample cell 13 for containing a gas mixture to be analyzed. An infrared source 15 directs infrared energy into the sample cell through a rotating chopper wheel 17 for periodically interrupting the infrared energy at a predetermined frequency. An electrical signal is produced corresponding to infrared energy of at least one preselected wavelength by a detector 19 monitoring infrared energy passing through the sample cell and a respective filter 21. Processing circuitry 23 is interconnected with the detector for receiving the signal from the detector and converting it into an output signal for indicating the concentration of a preselected gas within the sample cell.

Further details concerning construction of such an analyzer as well as the components for the processing circuitry are described in the references noted above. Accordingly, operation of the analyzer and circuitry is described only briefly below. In any event, it is to be noted that corresponding components within the analyzer and a separate channel of processing circuitry are provided for each gas monitored by the analyzer.

The signal produced by the detector 19 is an AC signal of an amplitude proportional to the infrared energy passing through the sample cell at that preselected wavelength and having a frequency corresponding to the predetermined frequency established by the chopper wheel 17. The preselected wavelength corresponds to the characteristic absorption wavelength for the preselected gas which is to be detected in the sample cell. The AC signal output of the detector is processed by the circuitry 23 to produce a DC signal having an amplitude proportional to the concentration of the gas to be detected. The signal is full-wave rectified and applied to an output amplifier 25 after initially passing into a preamplifier 27 forming an initial processing component for the circuitry 23. The output signal amplitude from the output amplifier 25 provides an indication of the concentration for each preselected gas within the sample cell. As described within the references set forth above, the processing circuitry 23 may be provided with various adjustments for calibrating its components in order to provide an accurate indication for each gas monitored within the sample cell.

In accordance with the present invention, the preamplifier 27 includes means to compensate for temperature variations within the detector 19. Similarly, the output amplifier 25 includes means to compensate for temperature variations within the sample cell 13. The manner in which these functions are carried out by the present invention is made apparent in the description set forth below. However, it is again noted that the analyzer may include one or more additional sets of components within the analyzer and additional processing channels corresponding to the circuitry 23 in order to permit monitoring of more than one predetermined gas within the sample cell 13.

Referring particularly to FIG. 1, the analyzer 11 is adapted for detecting two different gases within a gas mixture contained in or passed through the sample cell 13. The sample cell 13 is of tubular construction with closures 29 and 31 at opposite ends which are transparent to infrared radiation. Inlet and outlet means 33 and 35 are also interconnected with the sample cell 13 for passing a gas sample therethrough. The infrared source 15 is mounted within a housing 37 in communication with one end of the sample cell 13 by means of a window 39. The window 39 is formed of a material such as sapphire or mica which is substantially transparent to infrared radiation at wavelengths of interest while also providing a closure for the housing 37. A reflector 41 is mounted opposite the source 15 from the window 39 and the sample cell 13. The chopper wheel 17 is rotated between the window 39 and the sample cell 13 while having openings 43 arranged for alignment therebetween in order to selectively interrupt passage of infrared radiation into the sample cell in the manner described above.

Infrared radiation passing through the sample cell 13 is affected by the gas concentration within the sample cell. The resulting infrared radiation passes from the sample cell through the filter 21 for interaction with the detector 19, the detector producing an output signal which is applied to the processing circuitry 23 through a conduit 45.

The analyzer 11 also includes a second detector 19' for receiving infrared radiation from the sample cell through a second filter 21' and applying its output signal to a corresponding conduit 45'. It is to be understood that the signal in the second conduit 45' may be processed by a combination of circuit components similar to that indicated at 23 but not shown herein for purposes of simplicity.

Considering more particularly components of the processing circuitry 23, and output signal from the detector 19, in the form of a square wave signal having a frequency established by rotation of the chopper wheel 17, varies between nearly zero and either a positive or negative voltage. This signal is applied to the preamplifier 27 in which the signal is suitably amplified and then passed to a further amplification stage 47 including filter means (not shown).

After the signal is amplified and filtered at 47, it passes through a full wave linear rectifier 49 and a four-pole filter 51 to produce a DC signal having an amplitude proportional to the output of the detector 19. This DC signal is then amplified by another amplifier 53 and applied to the output amplifier 25 in a manner described in greater detail below.

The present invention is particularly concerned with provision in the circuitry 23 of a component to compensate for temperature variations in the detector 19. Within the analyzer 11, this function is accomplished within the preamplifier 27 which is illustrated in greater detail within FIG. 2. In addition, the invention also particularly contemplates means compensating for temperature variations within the sample cell 13 and this function is preferably accomplished by means associated with the output amplifier 25. Those components of the analyzer are described in greater detail below.

Initially, referring to FIG. 2 as well as FIG. 1, the detector 19 is characterized by responsivity in the form of an output electronic signal corresponding to the optical signal input received from the sample cell 13. For example, the detector 19 may have a negative temperature coefficient of approximately $-0.4\%$ per degree Centigrade. Over an exemplary temperature range for the analyzer of zero to 40° C., this produces a 16% change in the detector's output signal which would otherwise appear as a 16% change in flux from the source 15 or a 16% change in the infrared radiation or flux from the source due to gas absorption with the sample cell 13. In any event, the temperature coefficient of the detector 19 would otherwise result in a substantial apparent error in the analyzer output.

In order to compensate for this temperature variation of the detector, the present invention contemplates a thermistor-resistor network 55 associated with or formed as part of the preamplifier stage 27. The preamplifier stage 27 includes an operational amplifier 57, the thermistor-resistor network 55 being interconnected between the negative terminal of the operational amplifier 57 and ground. The thermistor-resistor network includes a temperature-sensitive thermistor 59 coupled between the negative terminal of the operational amplifier 57 and ground, a variable resistor 61 being interconnected between the negative terminal of the operational amplifier 57 and a signal output conduit 63 interconnecting the preamplifier stage 27 with the combined amplifier and filter 47 (see FIG. 1). The thermistor 59 has a series resistor 65 and a parallel resistor 66 to compensate for the temperature coefficient of the detector 19 as described above. The resistor 61 is adjusted for a nominal 5 V DC level at the output of 53. This gain adjustment accommodates different detector responsivities (from detector to detector). Also the optical "throughput" is variable from unit to unit and resistor 61 normalizes this.

Resistors 65 and 66 are chosen to modify the temperature coefficient of the thermistor (nominally 4%/°C.) to that required by the system. The temperature coefficient of the detector is, for example, nominally 0.4%/°C. Therefore, resistors 65 and 66 are chosen in conjunction with the thermistor 59 to provide a temperature coefficient of resistance of 0.4%/°C. for the complete thermistor network 64. Since the resistance of resistor 61 is large compared to the composite resistance of network 64, the gain of amplifier 57 varies as the ratio of resistor 61 to the resistance of network 64.

Referring again particularly to FIG. 1, the output amplifier 25 includes simplified electronic span compensation means for eliminating affects of temperature variation within the sample cell 13. In normal operation, the voltage output of an operational amplifier 67 within the output amplifier assembly 25 is determined by the instant ratio of a feedback variable resistor 69 and an input variable resistor 71 for the negative terminal of the operational amplifier 67 as well as the magnitude of voltage applied to the output amplifier 25 from the preceding amplifier stage 53. The signal from the preceding amplifier stage 53 is a function of the gas concentration in the sample cell 13. With sample gas being withheld from the sample cell (zero condition), the input resistor 71 is adjusted so that current flowing through the resistor to a summing junction 73 is equal to current flowing through a biasing resistor 75. Current flowing through the biasing resistor 75 is derived from a reference voltage 77 while being of opposite polarity to the signal voltage at the signal input terminal for the negative input terminal of the operational amplifier 67. Thus, the input resistor 71 may be adjusted in order to establish a zero setting for the output of the amplifier stage 25 as detected for example by a meter (not shown) coupled to the output for the amplifier stage 25.

Additional biasing resistors 79 and 81 form a voltage divider from the reference voltage 77 to a temperature-sensitive diode 83 which is also connected to ground. A junction 85 between the resistors 79 and 81 is also connected to ground through a normally closed switch and with the negative terminal of the operational amplifier 67 by means of a variable resistor 89 and a biasing resistor 91. The positive input of the operational amplifier 67 is connected to ground by means of a biasing resistor 93.

In normal operation, the junction between the resistors 79 and 81 is shorted or grounded by the normally closed switch 87. When the switch 87 is opened, current flows through the divider network and through resistors 89 and 91 to the summing junction 73 for the amplifier.

Resistors 79 and 81 are chosen in conjunction with source 77 and diode 83 to provide a voltage at junction 85 which varies with temperature. Diode 83 varies at approximately $2.6 \times 10^{-3}$ volts per °C. Source 77 is fixed at 5 volts nominal. In particular, resistors 79 and 81 are chosen to provide a voltage at junction 85 which varies at $-0.33\%$ per °C. This voltage "tracks" the density change of the gas in cell 13. The temperature dependent voltage at junction 85 in conjunction with resistors 89, 91 and 69 provides an output voltage for the amplifier 67, when switch 87 is opened, that varies at $-0.33\%/°C$. With no gas in the cell and switch 87 open a "cal signal" is produced. As the temperature increases the cal signal decreases and is put back to the zero mark by resistor 69 which increases the span or gain for the gas.

The voltage at the junction 85 varies with temperature because of the temperature coefficient for the diode 83. Although the diode 83 is physically located apart from the sample cell 13, it is subject to similar ambient temperature changes. Accordingly, the temperature coefficient for the diode 83 tends to change similarly as ambient temperature for the sample cell 13 so that the output amplifier 25 serves to compensate for temperature variations in the sample cell.

In operation of the output amplifier section 25, the input resistor 71 is adjusted to a zero output setting with zero gas in the sample cell. The span control resistor 69 is then adjusted with a known concentration of gas in the sample cell 13 to produce a known output signal from the output amplifier 25. The electronic calibration resistor 89 is then adjusted to a calibration set point (without sample gas in the cell) in order to establish a calibration setting in the output of the amplifier section 25. Thereafter, at predetermined intervals or when desired, any change in ambient temperature conditions may be compensated for by opening the switch 87 to activate the electronic calibration signal and adjusting the span control resistor 69 to its original reference point as determined by the meter reading for the output of the amplifier 25.

Various modifications and changes are believed apparent within the analyzer of the present invention as described above. Accordingly, the scope of the invention is defined only by the following appended claims.

What is claimed:

1. In an infrared gas analyzer including a sample cell for containing a gas mixture to be analyzed, source means for directing infrared energy through the sample cell, means for periodically interrupting the infrared energy at a predetermined frequency, detector means responsive to infrared energy of at least one preselected wavelength for producing a signal representative of the infrared energy passing through the sample cell and having a frequency corresponding to the predetermined frequency, and signal processing means for processing the signal output of said detector means to produce an output signal having an amplitude proportional to the concentration of the preselected gas in the mixture being analyzed, the improvement comprising amplifier means forming part of the signal processing means for receiving the signal from the detector means, said amplifier means including temperature responsive means adapted to compensate for variations in the signal from the detector means resulting from a change in ambient temperature, and an output amplifier also forming part of the signal processing means, said output amplifier including a manually adjustable input resistor for establishing a zero setting in the output of said output amplifier, a variable feedback resistor for adjusting the span of said output amplifier, and temperature responsive calibration means coupled with said output amplifier for indicating signal change in said output amplifier due to temperature variation to permit readjustment of span by said variable feedback resistor.

2. The infrared gas analyzer of claim 1 wherein said amplifier means include an operational amplifier coupled with the processing means for receiving an input signal at one input terminal, said feedback variable resistor being coupled between the output of said operational amplifier and its other input terminal, and a thermistor and biasing resistor coupled in series between said other input terminal of the operational amplifier and ground.

3. The infrared gas analyzer of claim 1 or 2 wherein said output amplifier comprises a further operational amplifier having one of its input terminals coupled with the signal processing means through said adjustable input resistor, a further variable feedback resistor being coupled between the output of said further operational amplifier and its other terminal, temperature response calibration means coupled with a summing junction between said further operational amplifier, said temperature response calibration means including a variable temperature calibrating resistor coupled with said summing junction, and selectively operable means coupled with said calibrating resistor for indicating signal variation due to a change in ambient temperature.

4. In an infrared gas analyzer including a sample cell for containing a gas mixture to be analyzed, source means for directing infrared energy through the sample cell, means for periodically interrupting the infrared energy at a predetermined frequency, detector means responsive to infrared energy of at least one preselected wavelength for producing a signal representative of the infrared energy passing through the sample cell and having a frequency corresponding to the predetermined frequency, and signal processing means for processing the signal output of said detector means to produce an output signal having an amplitude proportional to the concentration of the preselected gas in the mixture being analyzed, the improvement comprising amplifier means forming part of the signal processing means for receiving the signal from the detector means, said amplifier means including temperature responsive means adapted to compensate for variations in the signal from the detector means resulting from a change in ambient temperature, said amplifier means comprising an operational amplifier coupled with the processing means for receiving an input signal at one of its terminals, a feedback variable resistor being coupled between the output of said operational amplifier and its other terminal, and a thermistor and biasing resistor coupled in series between the other terminal of said operational amplifier and ground.

5. In an infrared gas analyzer including a sample cell for containing a gas mixture to be analyzed, source means for directing infrared energy through the sample cell, means for periodically interrupting the infrared energy at a predetermined frequency, detector means responsive to infrared energy of at least one preselected wavelength for producing a signal representative of the infrared energy passing through the sample cell and having a frequency corresponding to the predetermined frequency, and signal processing means for processing the signal output of said detector means to produce an output signal having an amplitude proportional to the concentration of the preselected gas in the mixture being analyzed, the improvement comprising an output amplifier forming part of the signal processing means, the output amplifier including a manually adjustable input resistor for establishing a zero setting in the amplifier output, a variable feedback resistor for adjusting span of said output amplifier, and temperature responsive calibration means coupled with said output amplifier for indicating signal change in said output amplifier due to temperature variation to permit readjustment of span by said variable feedback resistor, said output amplifier comprising an operational amplifier having one of its input terminals coupled with the signal processing means through an adjustable input resistor, said variable feedback resistor being coupled between the output of said operational amplifier and its other input terminal, said temperature responsive calibration means being coupled with a summing junction between said operational amplifier, said temperature responsive calibration means including a variable temperature calibrating resistor coupled with said summing junction, and selectively operable means coupled with said calibrating resistor for indicating signal variation due to a change in ambient temperature.

* * * * *